United States Patent
Burgi et al.

(10) Patent No.: US 9,772,319 B2
(45) Date of Patent: Sep. 26, 2017

(54) INTEGRATED METAL OXIDE CHEMICAL SENSOR

(71) Applicant: Sensirion AG, Stafa (CH)

(72) Inventors: Lukas Burgi, Zurich (CH); Marc Von Waldkirch, Zurich (CH); Felix Mayer, Stafa (CH)

(73) Assignee: Sensirion AG, Stafa (CH)

( * ) Notice: Subject to any disclaimer, the term of this patent is extended or adjusted under 35 U.S.C. 154(b) by 331 days.

(21) Appl. No.: 14/338,572

(22) Filed: Jul. 23, 2014

(65) Prior Publication Data
US 2015/0033827 A1 Feb. 5, 2015

(30) Foreign Application Priority Data
Jul. 30, 2013 (EP) .................................. 13003798

(51) Int. Cl.
*G01N 7/00* (2006.01)
*G01N 9/00* (2006.01)
*H01L 27/14* (2006.01)
*G01N 33/00* (2006.01)
*G01N 27/04* (2006.01)
*G01N 27/12* (2006.01)

(52) U.S. Cl.
CPC ......... *G01N 33/0027* (2013.01); *G01N 27/04* (2013.01); *G01N 27/122* (2013.01); *G01N 27/128* (2013.01)

(58) Field of Classification Search
CPC .. G01N 33/0027; G01N 27/127; G01N 27/14; G01N 27/4141; G01N 33/005; G01N 27/04; H01L 2924/0002; H01L 2924/00; H01L 2924/00014; H01L 2924/181; H01L 2924/00012

USPC .......................................... 73/31.06; 257/414
See application file for complete search history.

(56) References Cited

U.S. PATENT DOCUMENTS

| | | | | |
|---|---|---|---|---|
| 5,821,402 A * | 10/1998 | Okajima | ................. | C23C 16/04 422/90 |
| 6,763,710 B2 * | 7/2004 | Mayer | ................... | G01F 1/6845 73/204.11 |
| 6,888,358 B2 * | 5/2005 | Lechner | ................... | G01K 7/34 324/444 |
| 2004/0213701 A1 * | 10/2004 | Hattori | ................. | G01N 27/125 422/98 |
| 2010/0180668 A1 * | 7/2010 | Kruse | ................ | G01N 15/0656 73/28.01 |

(Continued)

FOREIGN PATENT DOCUMENTS

DE 10147107 9/2001

*Primary Examiner* — Eric S McCall
*Assistant Examiner* — Mohammed E Keramet-Amircola
(74) *Attorney, Agent, or Firm* — Cooper & Dunham LLP (57) ABSTRACT

A chemical sensor (10) is described with at least one layer of a metal oxide (11) arranged between two current injecting electrodes (16,16') with the length (L) of the layer of a metal oxide between the current injecting electrodes being less than 50 microns and one or a pair of voltage sensing electrodes (17) connected to the layer of a metal oxide (11) with the electrodes (16,16',17) forming a 3- or 4-terminal arrangement for determining the resistance changes of layer material (11) excluding series resistances such as contact resistances close to or at at least one of the current injecting electrodes (16) from the resistance measurement.

13 Claims, 6 Drawing Sheets

(56) References Cited

U.S. PATENT DOCUMENTS

| | | | | |
|---|---|---|---|---|
| 2011/0048970 A1* | 3/2011 | Sugaya | ................ | G01N 27/419 205/781 |
| 2011/0220820 A1* | 9/2011 | Burgi | ................... | G05D 7/0635 251/129.01 |
| 2013/0192338 A1* | 8/2013 | Mayer | ................ | G01N 33/4972 73/23.3 |
| 2013/0249499 A1* | 9/2013 | Graf | ................ | G01N 33/48785 320/150 |
| 2013/0344609 A1* | 12/2013 | Mayer | ................ | G01N 33/497 436/133 |
| 2014/0032153 A1* | 1/2014 | Mayer | ................ | G01N 33/0006 702/104 |

\* cited by examiner

FIG. 2  Reducing sensor dimensions

INTEGRATED METAL OXIDE CHEMICAL SENSOR

CROSS REFERENCE TO RELATED APPLICATIONS

This application claims the priority of European patent application 13003798.9, filed Jul. 30, 2013, the disclosure of which is incorporated herein by reference in its entirety.

FIELD OF THE INVENTION

The present invention relates to an integrated chemical sensor, particularly a gas sensor, using metal oxide. The sensor is sufficiently small to be located within the exterior shell or housing of a portable electronic device such as a mobile phone, tablet and the like.

BACKGROUND OF THE INVENTION

Portable or mobile devices originally introduced as mobile phones or electronic agendas become more and more ubiquitous. As the processing power of their internal processors grows and equally the bandwidth for communication with stationary processors, such portable devices take on more and more the role of multi-purpose tools available to consumers and specialist users alike.

It has been recognized that portable devices can benefit from the presence of sensors capable of providing a chemical analysis of materials brought into contact or the vicinity of the device. Whilst there are many possible applications for such sensors, it suffices to consider for example the analysis of air surrounding the portable device. Such an analysis can be useful for multiple purposes such as testing for hazardous gases, breath analysis for general medical purposes or driving fitness, and the like.

Known sensors for use as chemical sensor are metal oxide type sensors. In a metal oxide or MOX sensor a sensitive layer of a metal oxide is exposed to a fluid including the analyte. As the analyte is absorbed, the resistance across the layer changes. The change in resistance can be measured and converted into a concentration of the analyte in the fluid.

However integrating such a sensor within the narrow confines of a modern day portable device poses a significant technical challenge. Typically for such devices only a very limited volume is acceded to additional sensors outside the core functionality of the device such as wireless voice or data communication, display, speaker, processors and battery. This means that the real overall dimensions of the sensor, its associated circuitry for control and readout have to be within or close to the submillimeter range.

A sensor with these outer dimensions can only be manufactured, if the active structures, i.e. the size of the metal oxide film between electrodes, are reduced in length to below 50 microns or even less. However, in metal oxide sensors of this size the contact resistance caused by interface effects between the (metallic) contact electrodes and the metal oxide film contributes in ever larger proportion to the measurement, thus making it more difficult to measure actual changes in gas concentrations. The contact resistance may also be less stable over the life time of the sensors and, if not compensated for, increase the error in the measurement of the chemical sensor.

The four-terminal (4 T sensing), 4-wire sensing, or 4-point probes method is a known electrical impedance measuring technique that uses separate pairs of current-carrying and voltage-sensing electrodes to make more accurate measurements than traditional two-terminal (2 T) sensing. 4 T sensing is used in some ohmmeters and impedance analyzers and in precision wiring configurations for strain gauges and resistance thermometers. 4-point probes are also used to measure the sheet resistance of thin films. The four-terminal method is sometimes replaced by a three-terminal method, where one of each pair of electrodes is combined.

In the field of chemical gas sensors the German patent DE 10147107 C1 describes a four electrode structure within a gas sensitive layer. The resistance change in the layer between the outer electrodes is compared to the potential difference between the inner electrodes to detect the presence of a mixture of different gases.

It can be seen as an object of the invention to improve the chemical sensors using metal oxide films contacted through metallic electrodes, particularly for very small devices.

SUMMARY OF THE INVENTION

Hence, according to a first aspect of the invention, there is provided a chemical sensor comprising at least one layer of a metal oxide arranged between two current injecting electrodes with the length of the layer of a metal oxide between the current injecting electrodes being less than 50 microns and one or a pair of voltage sensing electrodes located at a current path between current injecting electrodes with the electrodes forming a 3- or 4-terminal arrangement for determining the resistance changes of layer material between the pair of voltage sensing electrodes by excluding series resistances in the current carrying path such as lead resistance and—particularly—the contact resistance at the interface between metal electrode and metal oxide sensing layer, which can occur at or close to at least one of the current injecting electrodes from the resistance measurement.

Typically but not exclusively the pair of voltage sensing electrodes is located in-between the location of the current injecting electrodes, and the voltage sensing electrodes are hence also referred to herein as inner electrodes and the current injecting electrodes as outer electrodes. The term "electrodes" as used herein is often limited to the terminals of the full electrodes within the area of the sensing layer or, in other words, the part of the electrodes which contribute to the measurement.

In a preferred variant the sensor comprises a voltmeter connected to the inner electrodes and arranged to determine a potential or voltage difference between the inner electrodes and a current meter within a circuit including the outer electrodes and arranged to measure the current flowing between the outer electrodes or a constant is current source thereby forming a resistance meter for determining the resistance changes of layer material between the pair of inner electrodes excluding the zone of layer material in the vicinity of the outer electrodes (and hence the lead resistance and—particularly—the contact resistance at the interface between metal electrode and metal oxide sensing layer) using the measured potential or voltage difference and current values. Reference to a measurement herein is seen as equivalent to the use of a voltage or currents source providing a known voltage or current. Changes in resistances are equivalent to changes in voltage or current as per Ohm's law.

The distance or length between the current injecting electrodes can be with the novel arrangement in the range of 1 to 50 µm, preferred in the range of 5 to 15 µm. In turn, the distance or length between the voltage sensing electrodes can be between 1 and 45 µm, preferably between 3 and 10 µm.

The vicinity of the current injecting electrodes is best defined using the distance between the inner and outer electrodes, which can be in the range of 1 to 5 µm, preferably in the range of 1 to 3 µm.

The width of an electrode itself can be in the range of 1 and 10 µm, preferably in the range of 1 to 3 µm.

In a preferred embodiment of the invention, a sensor in accordance with this invention is integrated as component within a portable electronic device having further uses other than chemical sensing. The portable device can be a smart phone, a handheld computer, a laptop, an electronic reader, a tablet computer, a game controller, a pointing device, a photo or a video camera, a digital music player, a wrist watch, a key fob, a head set or a computer peripheral. Its housing is typically a shell of metal, glass, or plastic material and can be assembled as a unibody or from several parts. Enclosed in the housing are typically processors, drivers for parts such as screens, antennae, cameras, microphones and speakers as well as batteries to provide power to the device and its parts. A screen is typically arranged as a part of the housing or mounted behind a transparent window of the housing.

In a preferred embodiment of the invention, a sensor in accordance with this invention is behind an opening with an area of less than 3 square millimeters providing a gas permeable access to a small duct within the housing.

The duct acts as confinement for the air inside the housing and can take the shape of a tube or channel formed as part of the housing or as a separate part connected to an opening in the housing. It can be a single straight or curved duct.

The opening itself can be a dedicated opening thus exclusively connecting the chemical sensor to the outside. However, given that the manufacturers of portable electronic devices strive to maintain the housing as a good protection against humidity and water, it is seen as advantageous that the opening is shared with at least one further component of the portable device requiring a similar connection to the exterior, such as a loudspeaker, a microphone or a camera. The opening can further be protected by a grill or a membrane to prevent bigger particles or unwanted components of the air from entering or blocking the duct.

The chemical sensor may be understood as a sensor device for detecting one or even more properties of one or more analytes. It is preferably based on one of the following measurement principles:

The sensor is best based on a metal-oxide such as tin oxide, tungsten oxide, gallium oxide, indium oxide, zinc oxide, not-intentionally doped or doped, or mixtures thereof, which preferably may be applied in a high temperature environment, i.e. operated at temperatures between 300 and 600° C.

The sensor is best integrated with CMOS circuitry for control and read-out onto a common substrate.

The sensor has preferably heating elements in the vicinity of the layer of metal oxide. Even more preferably, the heating elements are embedded within or deposited on a common substrate used to integrate CMOS circuitry for control and read-out of the sensor, which the can also be used to operate the heating elements.

The above and other aspects of the present invention together with further advantageous embodiments and applications of the invention are described in further details in the following description and figures.

DETAILED DESCRIPTION

Figure 1A:
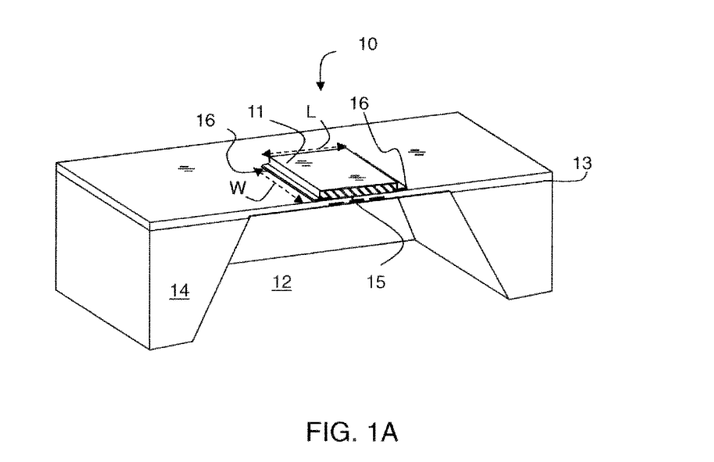
FIG. 1A is a schematic perspective view of a known metal oxide gas sensor.
Figure 1B:
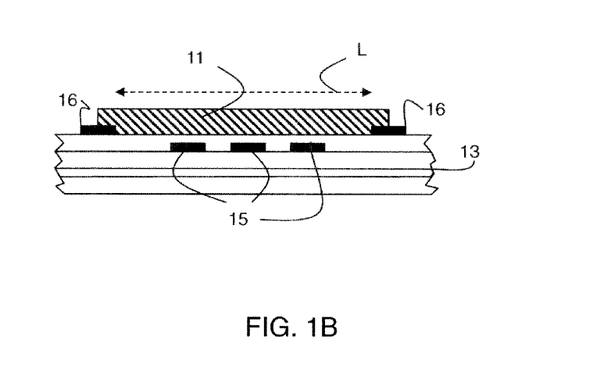
FIG. 1B is schematic cross-section of the device of FIG. 1A.

A gas sensor 10 with a sensing layer 11 of metal oxide is shown in FIGS. 1A and 1B. The sensor is integrated with a CMOS circuitry (not shown) on a single chip. Parts of the CMOS layers 13 and handle layer 14 required for the CMOS circuit are etched away to form a MEMS device with a cavity 12 at the location of the sensor. The remaining layers 13 above the cavity 12 form a thin membrane to support the actual sensor 10.

Embedded within the layers 13 are conducting elements forming a heater 15 to provide a local source of heat to heat the metal oxide 11 during operation of the sensor. The membrane structure above the cavity 12 provides an inherent thermal insulation for the rest of the substrate with the CMOS circuit. Also, the temperature can rise rapidly around the metal oxide layer 11, while the thicker part of chip reacts due to its thermal inertia with a slower rise of temperature. By controlling the heater accordingly, the metal oxide can be heated to its operating temperature of 250 to 600 degrees Celsius while the temperature of the CMOS layer remains below the critical limit for operation, typically about 80 degrees Celsius.

The metal oxide layer 11 is contacted by two conductive electrodes 16 and hence acts as a resistor. In the presence of an analyte this resistance changes thereby providing a measure of the concentration of the analyte in the immediate vicinity of the metal oxide layer.

Figure 2:
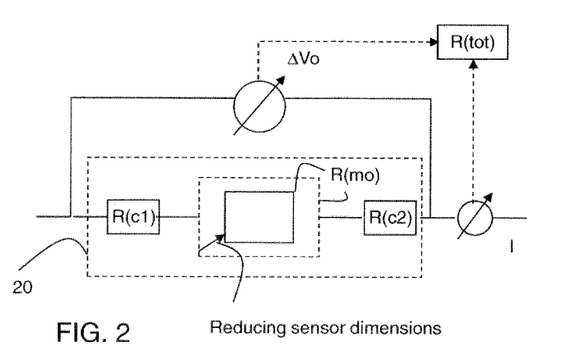
FIG. 2 is an equivalent circuit diagram for a metal oxide gas sensor with larger and smaller features.

The resistance R(tot) measured across the pair of electrodes 16 and the layer of metal oxide can be represented as the sum of three resistors in series as shown in the equivalent circuit diagram of FIG. 2. In this diagram the gas sensitive area is represented by the dashed box 20. The current flowing through the electrodes 16 and the layer 11 is a) either given by a constant current source or b) measured by a current meter I as shown. The voltage drop across the outer electrodes 16 is a) either measured by a voltmeter ΔVo as shown or b) given by a voltage source. In both cases a) and b) the total resistance R(tot) of the gas sensitive area is determined by combining the voltage and current values using Ohm's law.

This equivalent circuit diagram emphasizes the contribution to the total resistance R(tot) of the resistors R(c1) and R(c2) representing the contact resistance at the interfaces between the metal oxide layer 11 and the two electrodes 16.

In conventional metal oxide gas sensors the resistance R(mo) of the metal oxide layer is usually large and changes of it are readily accessible to the measurement without having regard to R(c1) and R(c2). However, as illustrated in FIG. 2 the relative contribution of R(c1) and R(c2) to the measured total resistance R(tot) grows as the size of the sensor 10 is reduced.

The size or dimension which is of importance for this aspect is the space between the electrodes 16, i.e. the inter-electrode distance, as bridged by the layer 11 of metal oxide and also referred to in this specification as the length L of the sensor. Referring also to the so-called width of an electrode, i.e. its lateral extension, as W, the resistances R(c1) and R(c2) are proportional to 1/W, whereas the resistance R(mo) is proportional to the ratio L/W. The proportion R(c)/R(mo) between both types of resistances varies hence with 1/L, i.e. the relative importance of interface effects increases with decreasing electrode separation L. In case of meandering or other complex shaped electrodes the length L is understood to be the minimal distance between the two electrodes. In the present example this characteristic dimension or width is assumed to be at least less than 50 microns or even less than 15 microns.

Figure 3A:
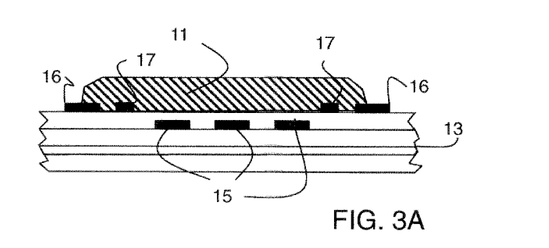
FIG. 3A is a schematic cross-section of a metal oxide gas sensor in accordance with an example of the invention.

Referring now to a sensor with a four electrode structure in accordance with an example of the invention and as shown in FIG. 3A, the electrodes 16 are now the outer electrodes used for current injection into the sensing layer 11. An additional pair of electrodes 17 has been introduced within the space defined by the outer electrodes 16. The additional pair of electrodes 17 is used to measure the voltage drop in the parts of the MOX layer 11 which are between the inner electrodes. Using circuitry with very high input impedance to measure said voltage drop a vanishingly small current is flowing through the interfaces between the inner electrodes and the MOX layer and thus the voltage drop measurement is not affected by the contact resistance.

Figure 3B:
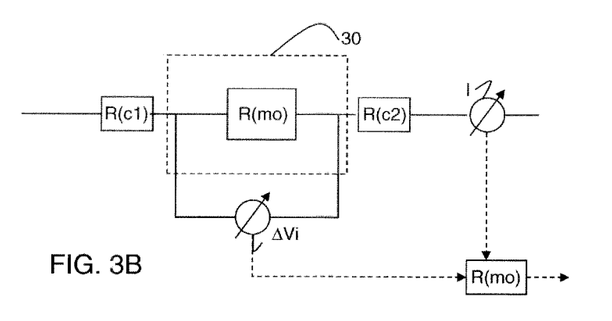
FIG. 3B is an equivalent circuit diagram for a metal oxide gas sensor as shown in FIG. 3A.

As illustrated in the equivalent circuit of FIG. 3B, this electrode and measurement arrangement avoids the contributions of the interface resistances R(c1) and R(c2). The resistance measured by combining the measurement of voltage drop across the inner electrodes 17 measured using the voltmeter ΔVi and the current through the circuit including the outer electrodes 16 as measured by the current meter I or determined by a constant current source is closer to the resistance change R(mo) within the sensing layer 11 itself and not influenced by the interface resistances R(c1) and R(c2).

As shown this method of measurement confined the sensing area 30 to a smaller region compared to the sensing area 20 of FIG. 2 above. The smaller sensing area 30 excludes the vicinity of the outer electrodes.

By determining R(mo) and R(tot) a measure can be gained representative of the contact resistance R(c1)+R(c2). In turn, the contact resistance or changes of the contact resistance over time can be indicative of either the presence of a mixture of gases as described for example in DE 10147107, or of long-term drifts in the material properties and hence be compensated for.

Figure 3C:
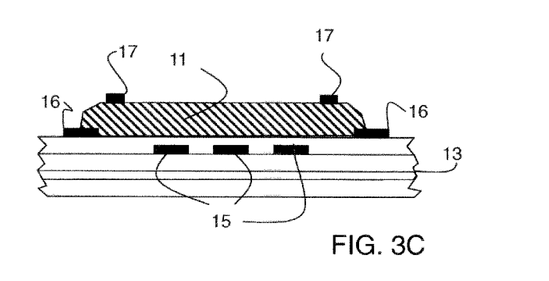
FIG. 3C is a schematic cross-section of an alternative embodiment of a metal oxide gas sensor in accordance with an example of the invention.

In gas sensors manufactured in a CMOS compatible process, it can be advantageous to vary the electrode arrangement. In FIG. 3A the inner and outer electrodes 16, 17 are deposited onto the same level of the substrate. In the variant of FIG. 3C, one set of the electrodes (here: the inner electrodes 17) are deposited onto the sensing layer 11. In this configuration the distance L between the inner electrodes 17 can be near, or almost equal to the same distance between the outer electrodes 16.

Figure 4A:
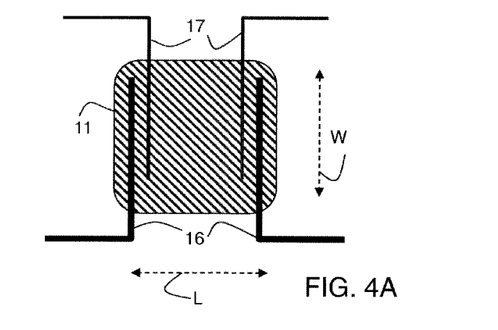
FIGS. 4A-4E illustrate examples of a metal oxide gas sensor in accordance with further examples of the invention.
Figure 4B:
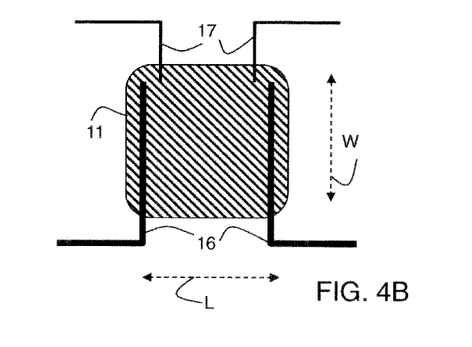
Figure 4C:
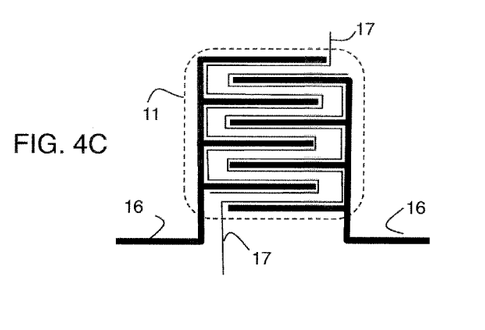

Further examples as illustrated in FIGS. 4A to 4C show possible arrangements of the inner and outer electrodes 16, 17 in a horizontal view thus providing an illustration of the possible lateral extensions of the electrodes 16, 17 as embedded within or deposited below or above the sensing layer 11.

In FIG. 4A the inner electrodes 17 run to a large extent in parallel to the outer electrodes 16, i.e., have essentially the same width W.

But as the inner electrodes 17 are designed for an essentially current-free measurement their dimensions can be chosen differently. For example in the configuration of FIG. 4B the inner electrodes 17 provide essentially short contact points to sense or sample the potential of the sensing layer 11 at those points.

An electrode arrangement with fingering outer electrodes 16 and meandering inner electrodes 17 located in the space between the outer electrodes is shown in FIG. 4C.

Figure 4D:
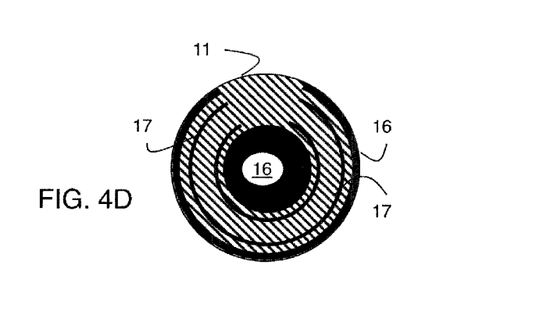

The electrode arrangement can also be configured to generate a radial current. In FIG. 4D one of the outer electrodes 17 is located at a central position with respect to the lateral dimensions of the sensing layer 11. The other outer electrode 17 is located at the circumference of the sensing layer 11. The inner electrodes 17 are located in the space between the outer electrodes 16.

Figure 4E:
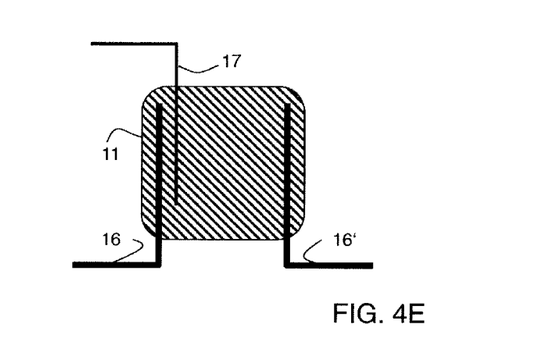

As an alternative to the four-terminal measurements described above, one of each pair of electrodes can be combined resulting in a three-terminal measurement of the resistance. Such an electrode arrangement is shown in FIG. 4E. In FIG. 4E one of the inner electrodes 17 is replaced or merged with one of the outer electrodes 16 and the voltage drop across the sensing layer 11 is measured between the remaining electrode 17 and the merged outer electrode 16'. This alternative can be advantageous, in case the processes of charge carrier injection into and extraction out of the MOX layer are asymmetric, e.g., if an energy barrier exists for injection but none for extraction. Thus the contact resistance can be highly asymmetric and can possibly be neglected at one electrode, i.e. the one where the outer electrode is also used as inner electrode for the method as described above.

The electrodes and MOX layer can be manufactured using methods known per se such as physical or chemical deposition from a vapor phase, sputtering, and casting. Alternatively a contact-free printing method can be used, e.g. an inkjet printing method, with several layers deposited onto each other (after a suitable drying period). In order to create larger areas, dots of one material, e.g. of electrode material or MOX material, can be deposited next to each other in an overlapping manner.

Any structures in the electrodes can be generated using for example a wet or dry etching process, by performing the deposition process through a mask or by using a deposition process capable of writing lines with the required resolution.

The material of the electrodes is typically a metal, for example Pt, Au, Al or W and their alloys. The metal-oxide used can be tin oxide, tungsten oxide, gallium oxide, indium oxide, or zinc oxide or mixtures thereof in either not-intentionally doped or doped form.

Figure 5A:
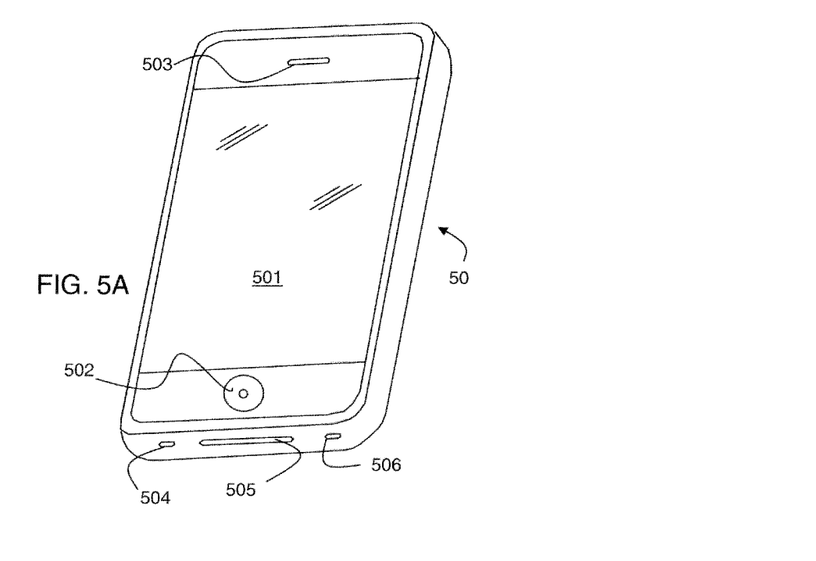
FIGS. 5A-5B illustrate a device in accordance with an example of the invention in a mobile electronic device.
Figure 5B:
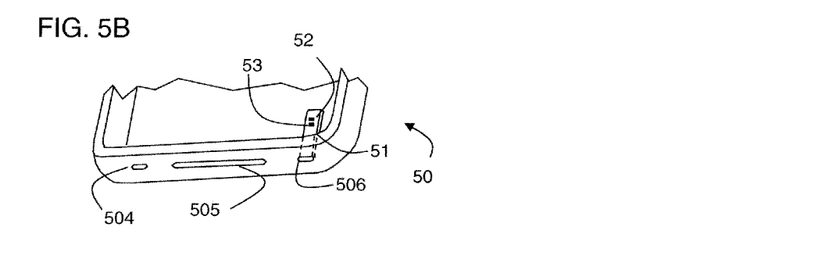

A chemical sensor in accordance with above can be for example part of a portable electronic device such as a mobile phone as shown in FIGS. 5A and 5B. As described above the chemical sensor needs to be of a (sufficiently small) size to fit within the limited volume available.

In FIG. 5A, the housing 50 of the mobile phone includes a front side with a screen 501 and elements like buttons 502 to let a user interact with the phone. Also shown on the front side is an opening 503 for a loudspeaker. Further openings 504,505 are located at a lower side wall of the housing 50. It is well known to mount components like microphones and loudspeakers behind such openings.

Another opening 506 is located at the lower side wall. As shown in FIG. 5B the opening 506 is linked to a tubular duct 51 passing through the interior of the housing. A chemical sensor 52 and a humidity sensor 53 are both mounted along the duct 51 such that the sensitive areas of both sensors are essentially exposed air of the same composition entering the duct through the opening 506. The actual size and shape of the duct 51 depends on the volume available and the nature of the chemical sensor 52 and the humidity sensor 53, but given the physical constraints of portable mobile devices the diameter of the opening is typically in the range of less than 2 mm and in the present example actually about 1 mm.

The chemical sensor 52 is a sensor in accordance with the examples described above and both it and the humidity sensor 53 can be manufactured as described for example in the cited application WO 2012/100362 or in WO 95/19563. The humidity sensor is best combined with a temperature sensor. Such sensors are commercially available, e.g. from Sensirion™ under the trade name SHTC1. The SHTC1 sensor measures 2 mm×2 mm×0.8 mm. Both sensors are mounted adjacent to each other in the duct 51.

While there are shown and described presently preferred embodiments of the invention, it is to be understood that the invention is not limited thereto but may be otherwise variously embodied and practised within the scope of the following claims.

The invention claimed is:

1. A chemical sensor comprising at least one layer of a metal oxide arranged between two current injecting electrodes with the length (L) of the layer of a metal oxide between the current injecting electrodes being less than 50 microns, and one separate voltage sensing electrode or a pair of separate voltage sensing electrodes connected to the layer of a metal oxide with the electrodes forming a 3- or 4-terminal arrangement for determining the resistance changes of layer material excluding contact resistances at the interface between the layer of metal oxide and at least one of the current injecting electrodes from the resistance measurement, the sensor further comprising
 a voltmeter ($\Delta$Vi) connected to the one separate voltage sensing electrode or to the pair of separate voltage sensing electrodes and arranged to determine a potential or voltage difference between the one separate voltage sensing electrode and one of the current injecting electrodes or between the pair of separate voltage sensing electrodes;
 and a current meter (I) or a constant current source within a circuit including the current injecting electrodes and arranged to determine the current flowing between the current injecting electrodes through the layer of metal oxide, thereby forming a resistance meter (R(mo)) for determining the resistance changes of layer material between the one separate voltage sensing electrode and one of the current injecting electrodes or between the pair of separate voltage sensing electrodes.

2. The chemical sensor according to claim 1, wherein the length (L) is less than 15 microns.

3. The chemical sensor according to claim 1, wherein the width (W) of the voltage sensing electrodes is less than half of the width (W) of the current injecting electrodes.

4. The chemical sensor according to claim 1, wherein the voltage sensing electrodes and the current injecting electrodes are arranged on opposite surfaces of the metal oxide layer.

5. The chemical sensor according to claim 1, wherein one of the current injecting electrodes forms a center electrode with the other of the current injecting electrodes located in the vicinity of the circumference of the metal oxide layer and the voltage sensing electrodes being arranged in the space between the current injecting electrodes.

6. The chemical sensor according to claim 1, further linked to a unit to determine the excluded series resistances or an equivalent thereof.

7. The chemical sensor according to claim 1, being integrated with a CMOS circuit onto a common substrate.

8. The chemical sensor according to claim 1, comprising heating elements to heat the metal oxide layer to an operating temperature, wherein the heating elements are part of a MEMS-type structure.

9. A portable electronic device comprising a chemical sensor in accordance with claim 1.

10. The portable electronic device according to claim 9, being selected from a group comprising:
 a mobile phone,
 a handheld computer,
 an electronic reader,
 a tablet computer,
 a game controller,
 a pointing device,
 a photo or a video camera,
 a digital music player,
 a wrist watch,
 a key fob,
 a head set, and
 a computer peripheral.

11. A method of operating a chemical sensor, comprising the steps of arranging at least one layer of a metal oxide between two current injecting electrodes with the length (L) of the layer of a metal oxide between the current injecting electrodes being less than 50 microns and connecting one separate voltage sensing electrode or a pair of separate voltage sensing electrodes to the layer of a metal oxide and using a voltmeter ($\Delta$Vi) to determine a potential or voltage difference between the one separate voltage sensing electrode and one of the current injecting electrodes or between the pair of separate voltage sensing electrodes, and a current meter (I) or a constant current source within a circuit including the current injecting electrodes to determine the current flowing between the current injecting electrodes through the layer of metal oxide and using the measured potential or voltage difference and current to determine the resistance changes of layer material between the one separate voltage sensing electrode and one of the current injection electrodes or between the pair of separate voltage sensing electrodes excluding contact resistances at the interface between the layer of metal oxide and at least one of the current injecting electrodes.

12. The method of claim 11, further including the step of determining the excluded contact resistances.

13. The method of claim 11, wherein contact resistances at one of the current injecting electrodes are neglected and said electrode is also used as one of the voltage sensing electrodes.

* * * * *